(12) United States Patent
Miyata et al.

(10) Patent No.: US 7,504,518 B2
(45) Date of Patent: Mar. 17, 2009

(54) PROCESS FOR PRODUCING BLOCKED ISOCYANATE COMPOUND

(75) Inventors: Hideo Miyata, Kawasaki (JP);
Masatoshi Murakami, Kawasaki (JP);
Katsutoshi Ohno, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 11/666,696

(22) PCT Filed: Oct. 27, 2005

(86) PCT No.: PCT/JP2005/020151
§ 371 (c)(1),
(2), (4) Date: Apr. 30, 2007

(87) PCT Pub. No.: WO2006/046758
PCT Pub. Date: May 4, 2006

(65) Prior Publication Data
US 2007/0265454 A1    Nov. 15, 2007

Related U.S. Application Data

(60) Provisional application No. 60/625,951, filed on Nov. 9, 2004.

(30) Foreign Application Priority Data
Oct. 29, 2004    (JP)    .............. 2004-316577

(51) Int. Cl.
C07D 231/00    (2006.01)
C07D 231/10    (2006.01)

(52) U.S. Cl. .............. 548/374.1; 548/356.1; 548/373.1

(58) Field of Classification Search .............. 548/356.1, 548/373.1, 374.1
See application file for complete search history.

(56) References Cited

U.S. PATENT DOCUMENTS

| 4,332,965 A | 6/1982 | Dalibor |
| 4,373,081 A | 2/1983 | Nachtkamp et al. |
| 5,246,557 A | 9/1993 | Hughes et al. |
| 5,395,721 A | 3/1995 | Kato et al. |
| 5,567,762 A | 10/1996 | Coyard et al. |
| 5,626,996 A | 5/1997 | Kato et al. |

FOREIGN PATENT DOCUMENTS

| EP | 0 713 871 A1 | 5/1996 | | |
| JP | 52-116420 | 9/1977 | | |
| JP | 57-121065 A | 7/1982 | | |
| JP | 3-17116 A | 1/1991 | | |
| JP | 06-75404 | 3/1994 | | |
| JP | 7-304843 A | 11/1995 | | |
| JP | 8-104726 A | 4/1996 | | |
| JP | 8-225509 A | 9/1996 | | |
| JP | 10-316663 A | * 12/1998 | .................. | 514/183 |
| JP | 10-316663 A | 12/1998 | | |

* cited by examiner

*Primary Examiner*—Kamal A Saeed
*Assistant Examiner*—Samantha L Shterengarts
(74) *Attorney, Agent, or Firm*—Sughrue Mion, PLLC

(57) ABSTRACT

Disclosed is a process for producing a blocked isocyanate compound represented by general formula (III): wherein $R^1$, $R^2$, $Q^1$, and $Q^2$ are as defined in the specification, characterized by comprising reacting a pyrazole compound (I) with an ethylenically unsaturated group-containing isocyanate compound (II) at a temperature in the range of 0° C. to 90° C. The production process can efficiently produce a high-purity blocked isocyanate compound without substantially producing by-products. In the production process, unlike the prior art technique, since there is no need to use any inert solvent such as toluene or xylene, safety to the human body and environment is excellent and the production processes and equipment can be simplified. The blocked isocyanate compound produced by the production process contains no residual inert solvent and is suitable for use in extensive fields such as various coating agents, adhesives, and molding materials.

13 Claims, 1 Drawing Sheet

PROCESS FOR PRODUCING BLOCKED ISOCYANATE COMPOUND

CROSS-REFERENCE TO RELATED APPLICATION

This application is an application filed under 35 U.S.C. § 111(a) claiming benefit pursuant to 35 U.S.C. § 119(e)(1) of the filing date of Provisional Application 60/625,951 filed Nov. 9, 2004 pursuant to 35 U.S.C. § 111(b).

FIELD OF THE INVENTION

The present invention relates to a process for producing a blocked isocyanate compound, which is a blocked form of an ethylenically unsaturated group-containing isocyanate, suitable for use as starting monomers of various coating agents, adhesives, and molding materials. More particularly, the present invention relates to a production process that can produce a high-purity blocked isocyanate compound on a commercial scale while avoiding the production of by-products caused by polymerization and the like.

BACKGROUND OF THE INVENTION

Blocked isocyanate compounds are compounds produced by reacting an isocyanate group with an active hydrogen group-containing compound (a blocking agent) to render the compounds inert at room temperature. Upon heating of the blocked isocyanate compounds, the blocking agent is dissociated, and the isocyanate group is regenerated. By virtue of this property, when the isocyanate group in a curing agent is blocked, the isocyanate compounds can be previously blended with an active hydrogen group-containing main agent and thus have been extensively used in coating agents, adhesives, molding materials and the like.

Conventional blocking agents for blocking the isocyanate group include alcohols, phenols, lactams, oximes, alkyl acetoacetate, alkyl malonates, phthalimides, imidazoles, hydrogen chloride, hydrogen cyanide, and sodium hydrogensulfite. Blocked isocyanate compounds produced by blocking the isocyanate group by, among the above blocking agents, substituted phenols, oximes, alkyl acetoacetates, alkyl malonates, phthalimides, imidazoles, hydrogen chloride, hydrogen cyanide, or sodium hydrogensulfite, cause dissociation at relatively low temperatures to regenerate the isocyanate group. For example, according to patent document 1, for hexamethylene diisocyanate blocked by the following compounds, the dissociation temperature upon heating for 20 min is as follows.

n-Butanol: about 170° C.
Phenol: about 160° C.
Caprolactam: about 160° C.
Methyl ethyl ketone oxime: about 150° C.
Acetoacetic ester: about 140° C.
Diethyl malonate: about 130° C.

Regarding the blocked isocyanate compounds produced by blocking the isocyanate group with blocking agents, for example, patent document 2 exemplifies polyblocked isocyanate compounds produced using 1,2,4-triazole and 3,5-dimethylpyrazole as the blocking agent, patent document 3 exemplifies polyblocked isocyanate compounds produced using an acetoacetic ester as the blocking agent, and patent document 4 exemplifies polyblocked isocyanate compounds produced using a diester of malonic acid as the blocking agent.

Regarding the reaction for blocking the isocyanate group with a pyrazole compound, for example, patent document 5 exemplifies a method in which polyisocyanate is reacted with 3,5-dimethylpyrazole in an organic solvent at 50° C. to 110° C., preferably 70° C. to 90° C., and patent document 6 exemplifies a method in which polyisocyanate is reacted with a pyrazole compound in an organic solvent at a temperature below 50° C. In the methods described in these patent documents, since the isocyanate group is reacted with the pyrazole compound in an organic solvent, these methods suffer from a problem that the solvent used in the reaction remains in the product after the reaction and, further, the removal of the solvent is difficult. Further, it should be noted that, in these patent documents, there is no description on a reaction of the blocking agent with a polymerizable compound such as an ethylenically unsaturated group-containing isocyanate compound.

Regarding the blocking of the isocyanate group in the ethylenically unsaturated group-containing isocyanate compound with a pyrazole compound, for example, patent document 7 exemplifies a method that comprises heating pyrazole or its derivative to a temperature at or above the melting point for melting, or dissolving or dispersing pyrazole or its derivative in an inert solvent such as toluene or xylene, and adding an ethylenically unsaturated group-containing compound or a solution of the compound dissolved in an inert solvent to the melt or the solution or dispersion. This method is advantageous in that the blocked isocyanate compound can be stably produced without causing polymerization of the blocked isocyanate compound and, at the same time, substantially no by-product is produced.

In the method described in patent document 7 in which pyrazole or its derivative is heated to a temperature at or above the melting point, however, pyrazole or its derivative is sublimated. Therefore, in order to allow the reaction to proceed smoothly, the use of an excessive amount of pyrazole or its derivative is necessary. This is disadvantageous from the viewpoint of productivity. Accordingly, a production process which can produce a blocked isocyanate compound with higher efficiency has been desired. On the other hand, in the method described in patent document 7 in which an inert solvent is used, the reaction can be carried out at relatively low temperatures, and, thus, advantageously, the sublimation of pyrazole or its derivative can be prevented and the reaction can proceed smoothly. Since, however, an inert solvent such as toluene or xylene is used, this method poses a problem of safety to the human body and environment and, at the same time, suffers from a problem of a complicated production process. Further, the removal of the inert solvent used in the reaction is difficult, and the solvent remains in the product. Therefore, there is a possibility that the blocked isocyanate compound thus obtained cannot be used, for example, in starting monomers of various coating agents, adhesives and molding materials. This has led to a demand for a production process of a blocked isocyanate compound that can eliminate the need to use any inert solvent.

Patent document 1: Japanese Patent Laid-Open No. 017116/1991
Patent document 2: Japanese Patent Laid-Open No. 304843/1995
Patent document 3: Japanese Patent Laid-Open No. 116420/1977
Patent document 4: Japanese Patent Laid-Open No. 121065/1982
Patent document 5: Japanese Patent Laid-Open No. 225509/1996
Patent document 6: Japanese Patent Laid-Open No. 104726/1996

Patent document 7: Japanese Patent Laid-Open No. 316663/1998

Accordingly, an object of the present invention is to provide a production process of a blocked isocyanate compound, that is, a production process of a blocked isocyanate compound comprising blocking an isocynate group in an ethylenically unsaturated group-containing isocyanate compound with a pyrazole compound, which production process can produce the compound with higher efficiency without the need to use any inert solvent.

DISCLOSURE OF INVENTION

As a result of extensive and intensive studies, the present inventors have found that the above problems of the prior art can be solved, which has led to the completion of the present invention.

The present invention will be summarized below.

[I] A process for producing a blocked isocyanate compound represented by general formula (III):

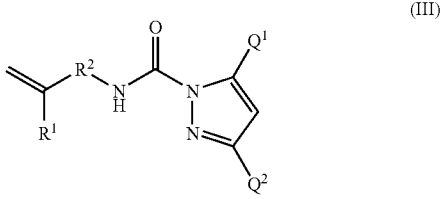

(III)

wherein $R^1$ represents a hydrogen atom or a methyl group; $R^2$ represents —CO— or —COOR$^3$— wherein $R^3$ represents an alkylene group having 2 to 6 carbon atoms; and $Q^1$ and $Q^2$ each independently represent a hydrogen atom, an alkyl group having 1 to 6 carbon atoms, RCONH—, or ROCO— wherein R represents an alkyl group having 1 to 6 carbon atoms, said process being characterized by comprising reacting a pyrazole compound (I) represented by general formula (I):

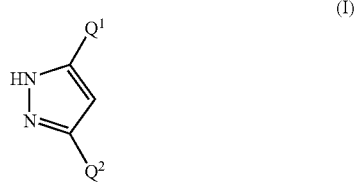

(I)

wherein $Q^1$ and $Q^2$ are as defined above, with an ethylenically unsaturated group-containing isocyanate compound (II) represented by general formula (II):

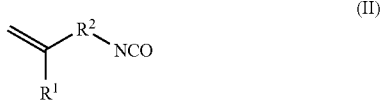

(II)

wherein $R^1$ and $R^2$ are as defined above,
at a temperature in the range of 0° C. to 90° C.

[2] The process according to the above item [1], characterized in that the blocked isocyanate compound (III) represented by general formula (III) is used as a solvent or a dispersant.

[3] The process according to the above item [2], characterized in that the ethylenically unsaturated group-containing isocyanate compound (II) is added to the pyrazole compound (I) dissolved or dispersed in the blocked isocyanate compound (III).

[4] The process according to the above item [2], characterized in that the ethylenically unsaturated group-containing isocyanate compound (II) dissolved or dispersed in the blocked isocyanate compound (III) is added to the pyrazole compound (I).

[5] The process according to the above item [2], characterized in that the ethylenically unsaturated group-containing isocyanate compound (II) dissolved or dispersed in the blocked isocyanate compound (III) is added to the pyrazole compound (I) dissolved or dispersed in the blocked isocyanate compound (III).

[6] The process according to the above item [2], characterized in that the pyrazole compound (I) is added to the ethylenically unsaturated group-containing isocyanate compound (II) dissolved or dispersed in the blocked isocyanate compound (III).

[7] The process according to the above item [2], characterized in that the pyrazole compound (I) dissolved or dispersed in the blocked isocyanate compound (III) is added to the ethylenically unsaturated group-containing isocyanate compound (II).

[8] The process according to the above item [2], characterized in that the pyrazole compound (I) dissolved or dispersed in the blocked isocyanate compound (III) is added to the ethylenically unsaturated group-containing isocyanate compound (II) dissolved or dispersed in the blocked isocyanate compound (III).

[9] The process according to the above item [2], characterized in that the pyrazole compound (I) dissolved or dispersed in the blocked isocyanate compound (III) and the ethylenically unsaturated group-containing isocyanate compound (II) dissolved or dispersed in the blocked isocyanate compound (III) are simultaneously added to a reactor.

[10] The process according to any one of the above items [1] to [9], wherein $Q^1$ and $Q^2$ represent an alkyl group having 1 to 5 carbon atoms.

[11] The process according to any one of the above items [1] to [10], wherein $R^2$ represent —COOR$^3$— wherein $R^3$ represents an alkylene group having 2 to 6 carbon atoms.

[12] The process according to any one of the above items [1] to [11], characterized in that the pyrazole compound (I) is reacted with the ethylenically unsaturated group-containing isocyanate compound (II) in the presence of a polymerization inhibitor.

[13] The process according to the above item [12], characterized in that the polymerization inhibitor is used in an amount of 10 to 20000 ppm based on the blocked isocyanate compound (III).

[14] The process according to any one of the above items [1] to [13], characterized in that the pyrazole compound (I) is reacted in an amount of 0.5 to 2.0 times by mole the amount of the ethylenically unsaturated group-containing isocyanate compound (II).

[15] A blocked isocyanate compound produced by the process according to any one of the above item [1] to [14], characterized in that the content of the ethylenically unsaturated group-containing isocyanate compound (II) remaining unreacted in the blocked isocyanate compound is not more than 1000 ppm.

[16] A blocked isocyanate compound produced by the process according to any one of the above items [1] to [14], characterized in that the content of the pyrazole compound (I)

remaining unreacted in the blocked isocyanate compound is zero or not more than 3% by weight.

According to the production process of the present invention, a blocked isocyanate compound can be produced with good efficiency. Further, since substantially no by-product is produced, a high-purity blocked isocyanate compound can be produced. Furthermore, in the production process according to the present invention, unlike the prior art technique, since there is no need to use any inert solvent such as toluene or xylene, safety to the human body and environment is excellent and the production processes and equipment can be simplified.

The blocked isocyanate compound produced by the production process contains no residual inert solvent and is suitable for use in extensive fields such as various coating agents, adhesives, and molding materials.

PREFERRED EMBODIMENTS OF THE INVENTION

Figure 1:
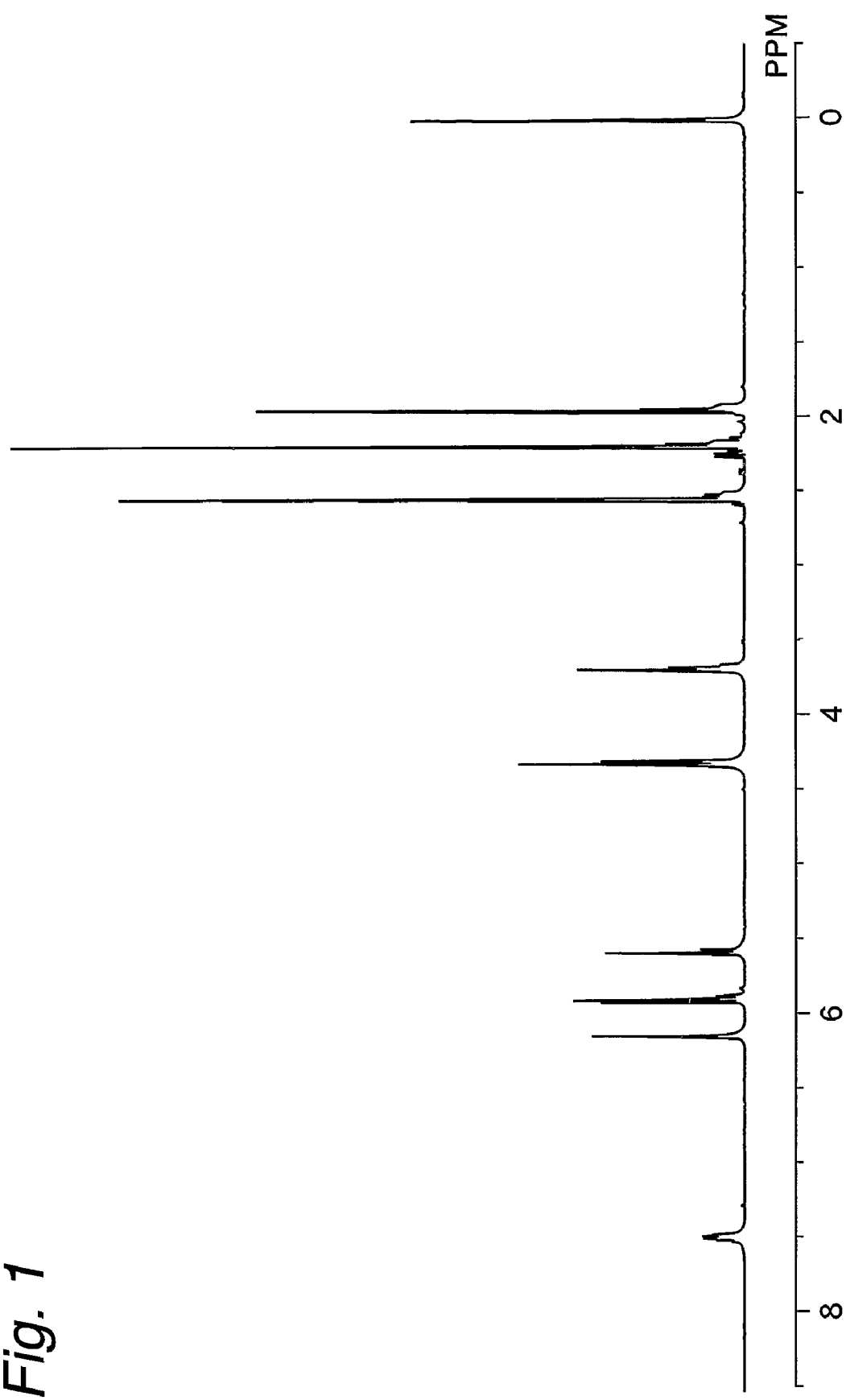
FIG. 1 is a $^1$H-NMR spectrum of a blocked isocyanate compound produced in Example 1.

The present invention will be described in more detail.

In a process according to the present invention for producing a blocked isocyanate compound (III) represented by general formula (III), a pyrazole compound (I) is reacted with an ethylenically unsaturated group-containing isocyanate compound (II) at a temperature in the range of 0° C. to 90° C.:

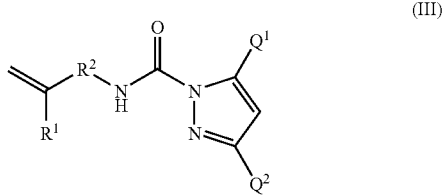

wherein $R^1$, $R^2$, $Q^1$, and $Q^2$ are as defined below.

In this production process, the pyrozole compound (I) as a starting compound is less likely to be sublimated. Therefore, there is no need to use an excessive amount of the starting compound, and, thus, the blocked isocyanate compound can be produced with good efficiency. Further, since substantially no by-product is produced, a high-purity blocked isocyanate compound can be produced. Furthermore, since there is no need to use any inert solvent, safety to the human body and environment is excellent, and the production processes and equipment can be simplified.

The pyrazole compound (I) used in the production process of the present invention is represented by general formula (I):

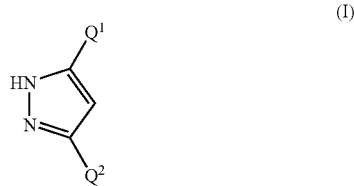

wherein $Q^1$ and $Q^2$ each independently represent a hydrogen atom, an alkyl group having 1 to 6 carbon atoms, RCONH—, or ROCO— wherein R represents an alkyl group having 1 to 6 carbon atoms, preferably an alkyl group having 1 to 5 carbon atoms. R preferably represents an alkyl group having 1 to 4 carbon atoms.

Various compounds, for example, unsubstituted pyrazole, 3,5-dimethylpyrazole, 3-acetylaminopyrazole, and diethyl pyrazole-3,5-dicarboxylate may be used as the pyrazole compound (I). Among them, 3,5-dimethylpyrazole is particularly preferred, for example, from the viewpoints of good availability and curability or other physical properties when it is used as a curable resin. The pyrazole compound (I) used in the present invention can be produced by the conventional process.

The ethylenically unsaturated group-containing isocyanate compound (II) used in the production process of the present invention is represented by general formula (II):

wherein $R^1$ represents a hydrogen atom or a methyl group; and $R^2$ represents —CO— or —COOR$^3$— wherein $R^3$ represents an alkylene group having 2 to 6 carbon atoms, preferably —COOR$^3$— wherein $R^3$ is as defined above.

Examples of the ethylenically unsaturated group-containing isocyanate compound (II) include 2-isocyanatoethyl (meth)acrylate, 3-isocyanatopropyl(meth)acrylate, 2-isocyanato-1-methyl ethyl(meth)acrylate, and methacryloyl isocyanate. The ethylenically unsaturated group-containing isocyanate compound (II) used in the present invention can be produced by the conventional method.

The blocked isocynate compound (III) according to the present invention is produced by reacting the pyrazole compound (I) with the ethylenically unsaturated group-containing isocyanate compound (II) at a temperature in the range of 0° C. to 90° C. The order of addition of these compounds is not particularly limited, and the blocked isocyanate compound (III) can be produced, for example, by the following methods: (1) a method in which a pyrazole compound (I) is charged into a reactor and an ethylenically unsaturated group-containing isocyanate compound (II) is added to the reactor with stirring to react the compound (I) with the compound (II); (2) a method in which an ethylenically unsaturated group-containing isocyanate compound (II) is charged into a reactor and a pyrazole compound (I) is added to the reactor with stirring to react the compound (I) with the compound (II); and (3) a method in which both a pyrazole compound (I) and an ethylenically unsaturated group-containing isocyanate compound (II) are simultaneously added to a reactor with stirring to react the compound (I) with the compound (II).

The temperature of the reaction of the pyrazole compound (I) with the ethylenically unsaturated group-containing isocyanate compound (II) may vary depending upon the types of the compound (I) and the compound (II). Preferably, however, the reaction temperature is below the melting point of the pyrazole compound (I) and is generally 0° C. to 90° C., preferably 5° C. to 70° C., more preferably 10° C. to 60° C. When the reaction temperature is in the above-defined range, the blocked isocyanate compound can be produced with good efficiency. Further, in this case, since substantially no by-product is produced, the purity of the resultant compound is high. Specifically, when the reaction temperature is below 0° C., the reaction rate is lowered and the lowered reaction rate affects the productivity and thus makes it impossible to produce the blocked isocyanate compound with good efficiency. On the other hand, when the reaction temperature is above 90° C., the pyrazole compound (I) is sublimated and, thus, the blocked isocyanate compound cannot be produced with good efficiency. Further, in this case, gelation is likely to occur due to polymerization of the ethylenically unsaturated group and, consequently, the blocked isocyanate compound (III) of high purity cannot be produced. The upper limit of the reaction temperature is preferably in such a temperature range that the pyrazole compound (I) is not sublimated, and is properly determined by the type of the pyrazole compound (I) used. This reaction temperature includes a reaction temperature during the addition of the pyrazole compound (I) and/or the ethylenically unsaturated group-containing isocyanate compound (II), for example, by dropping.

The reaction is generally carried out until the pyrazole compound (I) or the ethylenically unsaturated group-containing isocyanate compound (II) is substantially entirely consumed. Accordingly, the reaction time is not particularly limited. In general, however, the reaction time is about 30 min to 8 hr. The disappearance of the pyrazole compound (I) may be confirmed, for example, by the fact that, as a result of high speed liquid chromatography, the level of the compound (I) is below the detection limit. On the other hand, the disappearance of the ethylenically unsaturated group-containing isocyanate compound (II) may be confirmed, for example, by the fact that, as a result of IR measurement, the level of absorption based on NCO group is below the detection limit. It should be noted that the reaction time includes the time taken for the addition of the pyrazole compound (I) and/or the ethylenically unsaturated group-containing isocyanate compound (II), for example, by dropping.

In the production process of the present invention, the amount of the pyrazole compound (I) is 0.5 to 2.0 times by mole, preferably 0.8 to 1.5 times by mole, more preferably 1.0 to 1.2 times by mole, the amount of the ethylecially unsaturated group-containing isocyanate compound (II). The reaction ratio between these compounds is theoretically 1:1 (molar ratio). The reaction can be allowed to proceed smoothly by adding the compounds in the above-defined molar ratio. In the production process of a blocked isocyanate compound according to the present invention, since the reaction is carried out in the above-defined temperature range, the sublimation of the pyrazole compound (I) as a starting compound is less likely to occur. Therefore, unlike the prior art technique, there is no need to use the starting compound in an excess amount, and, thus, the blocked isocyanate compound can be produced with good efficiency and the starting compounds (I) and (II) remaining unreacted are not substantially present.

Further, in the reaction system, the addition of a polymerization inhibitor to the reaction system is preferred. The polymerization inhibitor is rapidly reacted with free radicals produced from monomers in the free-radical polymerization and thus can stabilize the reaction system so that the free-radical polymerization reaction does not proceed.

Commonly used polymerization inhibitors, for example, phenothiazine, p-methoxy phenol and 2,6-ditert-butyl-4-methylphenol(BHT), may be used as the polymerization inhibitor. The polymerization inhibitor can be introduced by any method without particular limitation, and examples of introduction methods usable herein include a method in which the polymerization inhibitor, together with the pyrazole compound (I), is introduced into a reactor, a method in which the polymerization inhibitor is dissolved in the ethylenically unsaturated group-containing isocyanate compound (II) and the resultant solution is then introduced into a reactor, a method in which the polymerization inhibitor is mixed to both the pyrazole compound (I) and the ethylenically unsaturated group-containing isocyanate compound (II) and these mixtures are each introduced into a reactor, and a method in which, after the completion of the reaction, the polymerization inhibitor is introduced into the resultant blocked isocyanate compound (III). In order to produce the blocked isocyanate compound (III) without causing the polymerization of the ethylenically unsaturated group-containing isocyanate compound (II) per se, the reaction of the pyrazole compound (I) with the ethylenically unsaturated group-containing isocyanate compound (II) in the presence of a polymerization inhibitor is preferred.

The amount of the polymerization inhibitor used varies depending upon the type of the pyrozole compound (I) and the ethylenically unsaturated group-containing isocyanate compound (II). Preferably, however, the amount of the polymerization inhibitor used is generally 10 to 20000 ppm, preferably 50 to 10000 ppm, more preferably 100 to 5000 ppm, based on the blocked isocyanate compound (III) produced by the reaction of the compound (I) with the compound (II). When the amount of the polymerization inhibitor used is less than 10 ppm, during the production of the blocked isocyanate compound (III), the polymerization of the ethylenically unsaturated group in the ethylenically unsaturated group-containing isocyanate compound (II) is likely to occur. On the other hand, when the amount of the polymerization inhibitor used exceeds 20000 ppm, the reactivity of the ethylenically unsaturated group, derived from the ethylenically unsaturated group-containing isocyanate compound (II), in the blocked isocyanate compound (III) is likely to be lowered.

The blocked isocyanate compound (III) represented by general formula (III) according to the present invention may be produced by the above process. A method may also be preferably adopted in which this blocked isocyanate compound (III) is used as a solvent or a dispersant and, in the medium, the blocked isocyanate compound (III) is further prepared.

When the blocked isocyanate compound (III) is used as the solvent or dispersant, the stirring efficiency can be improved and, thus, the reaction of the compound (I) with the compound (II) can be allowed to proceed smoothly. Further, since the reaction can be carried out at a relatively low temperature, the sublimation of the pyrazole compound (I) as the starting compound is less likely to occur. Accordingly, the reaction can be completed without the need to use the starting compound in an excess amount, and, thus, the blocked isocyanate compound can be produced with good efficiency. Further, since substantially no by-product is produced, a high-purity blocked isocyanate compound can be produced. Furthermore, unlike the prior art technique, since there is no need to use any inert solvent such as toluene or xylene, safety to the human body and environment is excellent and the production processes and equipment can be simplified.

The production of the compound (III) using the blocked isocyanate compound (III) as a solvent or a dispersant can be carried out, for example, by (1) a method in which a blocked isocyanate compound (III) and a pyrazole compound (I) are charged into a reactor, the pyrazole compound (I) is dissolved or dispersed, and an ethylenically unsaturated group-containing isocyanate compound (II) is then added to the reactor to react the compound (I) with the compound (II), (2) a method in which a pyrazole compound (I) is charged into a reactor, an ethylenically unsaturated group-containing isocyanate compound (II) dissolved or dispersed in a blocked isocyanate compound (III) is then added to the reactor to react the compound (I) with the compound (II), (3) a method in which a blocked isocyanate compound (III) and a pyrazole compound (I) are charged into a reactor, the pyrazole compound (I) is dissolved or dispersed, and an ethylenically unsaturated group-containing isocyanate compound (II) dissolved or dispersed in a blocked isocyanate compound (III) is then added to the reactor to react the compound (I) with the compound (II), (4) a method in which a blocked isocyanate compound (III) and an ethylenically unsaturated group-containing isocyanate compound (II) are charged into a reactor, the ethylenically unsaturated group-containing isocyanate compound (II) is dissolved or dispersed, and a pyrazole compound (I) is then added to the reactor to react the compound (I) with the compound (II), (5) a method in which an ethylenically unsaturated group-containing isocyanate compound (II) is charged into a reactor, and a pyrazole compound (I) dissolved or dispersed in a blocked isocyanate compound (III) is then added to the reactor to react the compound (I) with the compound (II), (6) a method in which a blocked isocyanate compound (III) and an ethylenically unsaturated group-containing isocyanate compound (II) are charged into a reactor, the ethylenically unsaturated group-containing isocyanate compound (II) is dissolved or disperse, and a pyrazole compound (I) dissolved or dispersed in a blocked isocyanate compound (III) is then added to the reactor to react the compound (I) with the compound (II), and (7) a method in which a pyrazole compound (I) dissolved or dispersed in a blocked isocyanate compound (III) and an ethylenically unsaturated group-containing isocyanate compound (II) dissolved or dispersed in a blocked isocyanate compound (III) are simultaneously added to a reactor to react the compound (I) with the compound (II).

When the blocked isocyanate compound (III) is produced by any one of the above methods (1) to (7), the fluidity of the starting compounds can be improved. Specifically, the starting compounds can easily be transferred even on a commercial scale to allow the reaction to proceed smoothly. Among the methods (1) to (7), the methods (1), (6) and (7) are particularly preferred.

When the blocked isocyanate compound (III) is used as the solvent or dispersant, the use of the same pyrazole compound (I) and ethylenically unsaturated group-containing isocyanate compound (II) as used in the production of the compound (III) is preferable.

When the blocked isocyanate compound (III) is used as the solvent or dispersant, the amount of the compound (III) used is not particularly limited. Preferably, however, the amount of the compound (III) used is 0.01 to 50 times by mole, preferably 0.01 to 10 times by mole, more preferably 0.01 to 5 times by mole, the amount of the pyrazole compound (I). When the amount of the compound (III) used is less than 0.01 time by mole, the contemplated effect as the solvent or dispersant cannot be attained, probably, for example, leading to a lowering in reaction rate, although no problem occur in the reaction. On the other hand, when the amount of the compound (III) used exceeds 50 times by mole, the productivity is sometimes lowered, although no problem occur in the reaction.

Even when the blocked isocyanate compound (III) is used as the solvent or dispersant, the reaction is carried out under the same conditions as the above methods, except that the compound (III) is used as the solvent or dispersant.

The above production process according to the present invention can provide a blocked isocyanate compound (III), according to the present invention, represented by general formula (III):

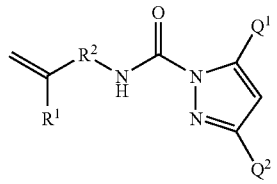

wherein $R^1$, $R^2$, $Q^1$, and $Q^2$ are as defined above.

The blocked isocyanate compound (III) according to the present invention may contain a small amount of impurities such as starting compounds remaining unreacted and the polymerization inhibitor as mentioned later. These impurities may be removed by any conventional method for the purification of the product.

In the production process of a blocked isocyanate compound (III) according to the present invention, since the reaction is allowed to proceed at the above temperature, the reaction proceeds smoothly without substantially causing sublimation of the pyrazole compound (I). Thus, according to the present invention, a high-purity blocked isocyanate compound (III), which does not contain or contains only a small amount (not more than 3% by weight) of the pyrazole compound (I) remaining unreacted or contains only a small amount (not more than 1000 ppm), of the ethylenically unsaturated isocyanate compound (II) remaining unreacted can be produced.

Further, in the production process of a blocked isocyanate compound (III) according to the present invention, since an inert solvent such as toluene or xylene is not used, the solvent does not remain in the blocked isocyanate compound (III). Therefore, the blocked isocyanate compound (III) can be advantageously used, for example, as starting monomers of various coating agents, adhesive, and molding materials.

EXAMPLES

The present invention will be described in more detail with reference to the following examples and comparative examples. However, it should be noted that the present invention is not limited to these examples. Measurement methods used in the following examples are as follows.

<Measurement Methods>

Measurement of Infrared Absorption Spectrum (Hereinafter Referred to as "IR Spectrum Measurement")

Instrument: infrared spectrophotometer FT/IR-8000, manufactured by JASCO International Co., Ltd.

Analytical method: transmission method (using KBr plate)

High Speed Liquid Chromatography (1) (Hereinafter Referred to as "LC Analysis (1)")

Column: Shodex Silica C18M 4E

Detector: 875-UV UV 220 nm, manufactured by JASCO International Co., Ltd.

Eluent: water/acetonitrile=65/35

Pump: Shodex DS-4
Flow rate: 1 ml/min
Integrator: C-R8A, manufactured by Shimadzu Corporation.
Oven: Shodex AO-50, 45° C.
Sample preparation: About 0.1 g of a sample was weighed into a 10-ml measuring flask, and the eluent was added to a predetermined volume.

High Speed Liquid Chromatography (2) (Hereinafter Referred to as "LC Analysis (2)")
Column: Shodex Silica SIL 10B
Detector: Shodex UV-41 UV 254 nm
Eluent: n-hexane/ethyl acetate=7/3
Pump: Shodex DS-4
Flow rate: 0.6 ml/min
Integrator: C-R7Aplus, manufactured by Shimadzu Corporation.
Oven: Shodex AO-50, 40° C.
Sample preparation: About 0.1 g of a sample was weighed into a 10-ml measuring flask, and the eluent was added to a predetermined volume.

Gas Chromatography (Hereinafter Referred to as "GC Analysis")
Analytical instrument: HP 6850, manufactured by HP
Column: DB-1 30 m×0.32 mm×1 μm, manufactured by J & W
Column temperature: 70° C.→rise to 250° C. at a rate of 10° C./min→holding for 18 min
Integrator: HP3396
Injection temperature: 250° C.
Detector temperature: 300° C. FID
Detector: FID, $H_2$ 40 ml/min, air 400 ml/min
Carrier gas: He 30 ml/min Measurement of Nuclear Magnetic Resonance Spectrum (Hereinafter Referred to as "NMR Measurement")
Instrument: JNM-400 manufactured by JEOL Ltd.
Solvent: $CDCl_3$ Example 1

3,5-Dimethylpyrazole (purity 99%, manufactured by Japan Hydrazine Company, Inc.; the same shall apply hereinafter) (19.81 g, 0.204 mol) and BHT (purity 99%, manufactured by Tokyo Kasei Kogyo Co., Ltd.; the same shall apply hereinafter) (0.2 g, 0.84 mmol) were charged into a 100-ml four-necked flask equipped with a stirrer, a thermometer, a dropping funnel, and a reflux condenser under a nitrogen atmosphere. The contents of the flask were cooled in a water bath of 15° C. with stirring. Next, 2-isocyanatoethyl methacrylate (Karenz MOI, manufactured by Showa Denko K.K.; the same shall apply hereinafter) (31.03 g, 0.2 mol) was added dropwise through the dropping funnel over a period of 90 min. Upon the dropwise addition, the internal temperature of the flask changed from 15° C. to 40° C. After the completion of the dropwise addition, stirring was continued at an internal temperature in the range of 30° C. to 40° C. for one hr while regulating the temperature in a water bath. A small amount of a sample was obtained from within the reaction system, and an IR spectrum was measured. As a result, the level of absorption around 2270 $cm^{-1}$ based on NCO group was below the detection limit, and absorption at 1720 to 1750 $cm^{-1}$ based on C=O group was observed. Accordingly, the reaction was stopped. The reaction solution was cooled to room temperature to give 51.1 g of a light-yellow transparent liquid product. The product was measured for $^1$H-NMR. As a result, it was found that a blocked isocyanate compound represented by the following formula was produced. The $^1$H-NMR spectrum is shown in FIG. 1.

As a result of LC analysis (1), it was found that the content of 3,5-dimethylpyrazole was 0.76% by weight. Further, the product was subjected to GC analysis and was found to have a BHT content of 4400 ppm.

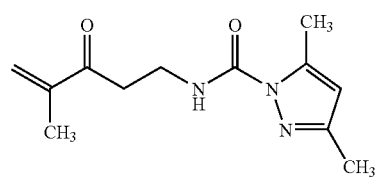

Example 2

The blocked isocyanate compound (17.09 g, 0.068 mol) synthesized by the process described in Example 1, 3,5-dimethylpyrazole (19.81 g, 0.204 mol), and BHT (0.2 g, 0.84 mmol) were charged into a 100-ml four-necked flask equipped with a stirrer, a thermometer, a dropping funnel, and a reflux condenser, and the contents of the flask were stirred at room temperature for one hr. Next, 2-isocyanatoethyl methacrylate (31.03 g, 0.2 mol) was added dropwise through the dropping funnel over a period of 90 min. Upon the dropwise addition, the internal temperature of the flask changed from 25° C. to 40° C. After the completion of the dropwise addition, stirring was continued at an internal temperature in the range of 30° C. to 40° C. for one hr while regulating the temperature in a water bath. A small amount of a sample was obtained from within the reaction system, and an IR spectrum was measured. As a result, the level of absorption around 2270 $cm^{-1}$ based on NCO group was below the detection limit, and absorption at 1720 to 1750 $cm^{-1}$ based on C=O group was observed. Accordingly, the reaction was stopped. The reaction solution was cooled to room temperature to give 67.9 g of a light-yellow transparent liquid product. The product was measured for $^1$H-NMR. As a result, it was found that the same blocked isocyanate compound as produced in Example 1 was produced. As a result of LC analysis (1), it was found that the content of 3,5-dimethylpyrazole was 0.76% by weight. Further, the product was subjected to GC analysis and was found to have a BHT content of 4400 ppm.

Example 3

The blocked isocyanate compound (17.09 g, 0.068 mol) synthesized by the process described in Example 1 and 2-isocyanatoethyl methacrylate (31.03 g 0.2 mol) were charged into a 100-ml flask, and the contents of the flask were stirred at room temperature for one hr to prepare solution A. 3,5-Dimethylpyrazole (19.81 g, 0.204 mol) and BHT (0.2 g, 0.84 mmol) were charged into a 100-ml four-necked flask equipped with a stirrer, a thermometer, a dropping funnel, and a reflux condenser, and solution A was added dropwise through the dropping funnel at room temperature with stirring over a period of 90 min. Upon the dropwise addition, a rise in internal temperature was observed. Specifically, the internal temperature of the flask changed from 25° C. to 40° C. After the completion of the dropwise addition, stirring was continued at an internal temperature in the range of 30° C. to 40° C. for one hr while regulating the temperature in a water bath. A small amount of a sample was obtained from within the reaction system, and an IR spectrum was measured. As a result, the level of absorption around 2270 cm$^{-1}$ based on NCO group was below the detection limit, and absorption at 1720 to 1750 cm$^{-1}$ based on C=O group was observed. Accordingly, the reaction was stopped. The reaction solution was cooled to room temperature to give 68.0 g of a light-yellow transparent liquid product. The product was measured for $^1$H-NMR. As a result, it was found that the same blocked isocyanate compound as produced in Example 1 was produced. As a result of LC analysis (1), it was found that the content of 3,5-dimethylpyrazole was 0.76% by weight. Further, the product was subjected to GC analysis and was found to have a BHT content of 4400 ppm.

Example 4

The blocked isocyanate compound (768.97 g, 3.06 mol) synthesized by the process described in Example 1 and 2-isocyanatoethyl methacrylate (31.03 g, 0.2 mol) were charged into a 1-L flask, and the contents of the flask were stirred at room temperature for one hr to prepare solution A. The blocked isocyanate compound (768.97 g, 3.06 mol) synthesized by the process described in Example 1, 3,5-dimethylpyrazole (19.81 g, 0.204 mol), and BHT (0.2 g, 0.84 mmol) were charged into a 2000-ml four-necked flask equipped with a stirrer, a thermometer, a dropping funnel, and a reflux condenser, and the contents of the flask were stirred at room temperature for one hr. Next, solution A was added dropwise through the dropping funnel over a period of 3 hr. Upon the dropwise addition, the internal temperature of the flask changed from 25° C. to 40° C. After the completion of the dropwise addition, stirring was continued at an internal temperature in the range of 30° C. to 40° C. for one hr while regulating the temperature in a water bath. A small amount of a sample was obtained from within the reaction system, and an IR spectrum was measured. As a result, the level of absorption around 2270 cm$^{-1}$ based on NCO group was below the detection limit, and absorption at 1720 to 1750 cm$^{-1}$ based on C=O group was observed. Accordingly, the reaction was stopped. The reaction solution was cooled to room temperature to give 1588.5 g of a light-yellow transparent liquid product. The product was measured for $^1$H-NMR. As a result, it was found that the same blocked isocyanate compound as produced in Example 1 was produced. As a result of LC analysis (1), it was found that the content of 3,5-dimethylpyrazole was 0.76% by weight. Further, the product was subjected to GC analysis and was found to have a BHT content of 4400 ppm.

Example 5

The blocked isocyanate compound (17.09 g, 0.068 mol) synthesized by the process described in Example 1, 2-isocyanatoethyl methacrylate (31.03 g, 0.2 mol), and BHT (0.2 g, 0.84 mmol) were charged into a 100-ml four-necked flask equipped with a stirrer, a thermometer, a dropping funnel, and a reflux condenser, and the contents of the flask were stirred at room temperature for one hr. Next, 3,5-dimethylpyrazole (19.81 g, 0.204 mol) was introduced by portions into the flask over a period of 90 min. Upon the introduction of 3,5-dimethylpyrazole, a rise in internal temperature was observed. Specifically, the internal temperature of the flask changed from 25° C. to 40° C. After the completion of the dropwise addition, stirring was continued at an internal temperature in the range of 30° C. to 40° C. for one hr while regulating the temperature in a water bath. A small amount of a sample was obtained from within the reaction system, and an IR spectrum was measured. As a result, the level of absorption around 2270 cm$^{-1}$ based on NCO group was below the detection limit, and absorption at 1720 to 1750 cm$^{-1}$ based on C=O group was observed. Accordingly, the reaction was stopped. The reaction solution was cooled to room temperature to give 67.9 g of a light-yellow transparent liquid product. The product was measured for $^1$H-NMR. As a result, it was found that the same blocked isocyanate compound as produced in Example 1 was produced. As a result of LC analysis (1), it was found that the content of 3,5-dimethylpyrazole was 0.76% by weight. Further, the product was subjected to GC analysis and was found to have a BHT content of 4400 ppm.

Example 6

2-Isocyanatoethyl methacrylate (31.03 g, 0.2 mol) and 0.3 g of BHT were charged into a 100-ml four-necked flask equipped with a stirrer, a thermometer, a dropping funnel, and a reflux condenser, and the contents of the flask were stirred with heating in a water bath of 50° C. for one hr. Separately, a blocked isocyanate compound (256.32 g, 1.02 mol) synthesized by the process described in Example 1 and 3,5-dimethylpyrazole (19.81 g, 0.204 mol) were stirred in another vessel at room temperature for one hr to prepare a slurry. This slurry was introduced into the flask through a plunger pump over a period of 120 min. Upon the introduction of the slurry, the internal temperature changed from 50° C. to 60° C. After the completion of the introduction, stirring was continued at an internal temperature in the range of 50° C. to 55° C. for one hr while regulating the temperature in a water bath. A small amount of a sample was obtained from within the reaction system, and an IR spectrum was measured. As a result, the level of absorption around 2270 cm$^{-1}$ based on NCO group was below the detection limit, and absorption at 1720 to 1750 cm$^{-1}$ based on C=O group was observed. Accordingly, the reaction was stopped. The reaction solution was cooled to room temperature to give 307.3 g of a light-yellow transparent liquid product. The product was measured for $^1$H-NMR. As a result, it was found that the same blocked isocyanate compound as produced in Example 1 was produced. As a result of LC analysis (1), it was found that the content of 3,5-dimethylpyrazole was 0.76% by weight. Further, the product was subjected to GC analysis and was found to have a BHT content of 4400 ppm.

Example 7

The blocked isocyanate compound (768.97 g, 3.06 mol) synthesized by the process described in Example 1 and 3,5-dimethylpyrazole (19.81 g, 0.204 mol) were charged into a 1-L flask, and the contents of the flask were stirred at room temperature for one hr to prepare slurry solution A. The blocked isocyanate compound (768.97 g, 3.06 mol) synthesized by the process described in Example 1, 2-isocyanatoethyl methacrylate (31.03 g, 0.2 mol), and BHT (0.2 g, 0.84 mmol) were charged into a 2000-ml four-necked flask equipped with a stirrer, a thermometer, a dropping funnel, and a reflux condenser, and the contents of the flask were stirred at room temperature for one hr. Next, slurry solution A was introduced through a plunger pump into the four-necked flask over a period of 3 hr. Upon the introduction of slurry solution A, the internal temperature changed from 25° C. to 40° C. After the completion of the dropwise addition, stirring was continued at an internal temperature in the range of 30° C. to 40° C. for one hr while regulating the temperature in a water bath. A small amount of a sample was obtained from within the reaction system, and an IR spectrum was measured. As a result, the level of absorption around 2270 cm$^{-1}$ based on NCO group was below the detection limit, and absorption at 1720 to 1750 cm$^{-1}$ based on C=O group was observed. Accordingly, the reaction was stopped. The reaction solution was cooled to room temperature to give 1588.5 g of a light-yellow transparent liquid product. The product was measured for $^1$H-NMR. As a result, it was found that the same blocked isocyanate compound as produced in Example 1 was produced. As a result of LC analysis (1), it was found that the content of 3,5-dimethylpyrazole was 0.76% by weight. Further, the product was subjected to GC analysis and was found to have a BHT content of 4400 ppm.

Example 8

The blocked isocyanate compound (768.97 g, 3.06 mol) synthesized by the process described in Example 1 and 3,5-dimethylpyrazole (19.81 g, 0.204 mol) were charged into a 1-L flask, and the contents of the flask were stirred at room temperature for one hr to prepare slurry solution A. The blocked isocyanate compound (768.94 g, 3.06 mol) synthesized by the process described in Example 1 and 2-isocyanatoethyl methacrylate (31.03 g, 0.2 mol) were charged into another 1-L flask, and the contents of the flask were stirred at room temperature for one hr to prepare solution B. BHT (0.2 g, 0.84 mmol) was charged into a 2000-ml four-necked flask equipped with a stirrer, a thermometer, a dropping funnel, and a reflux condenser. Slurry solution A and solution B were simultaneously added dropwise to the four-necked flask at room temperature with stirring over a period of 3 hr. Upon the dropwise addition, the internal temperature changed from 25° C. to 30° C. After the completion of the dropwise addition, stirring was continued at an internal temperature in the range of 30° C. to 40° C. for one hr while regulating the temperature in a water bath. A small amount of a sample was obtained from within the reaction system, and an IR spectrum was measured. As a result, the level of absorption around 2270 cm$^{-1}$ based on NCO group was below the detection limit, and absorption at 1720 to 1750 cm$^{-1}$ based on C=O group was observed. Accordingly, the reaction was stopped. The reaction solution was cooled to room temperature to give 1588.5 g of a light-yellow transparent liquid product. The product was measured for $^1$H-NMR. As a result, it was found that the same blocked isocyanate compound as produced in Example 1 was produced. As a result of LC analysis (1), it was found that the content of 3,5-dimethylpyrazole was 0.76% by weight. Further, the product was subjected to GC analysis and was found to have a BHT content of 4400 ppm.

Example 9

3,5-Dimethylpyrazole (29.13 g, 0.300 mol) and BHT (0.6 g, 2.54 mmol) were charged into a 100-ml four-necked flask equipped with a stirrer, a thermometer, a dropping funnel, and a reflux condenser under a nitrogen atmosphere, and the contents of the flask were cooled in a water bath of 15° C. with stirring. Next, 2-isocyanatoethyl methacrylate (31.03 g, 0.2 mol) was added dropwise through the dropping funnel over a period of 90 min. Upon the dropwise addition, the internal temperature of the flask changed from 15° C. to 40° C. After the completion of the dropwise addition, stirring was continued at an internal temperature in the range of 30° C. to 40° C. for one hr while regulating the temperature in a water bath. A small amount of a sample was obtained from within the reaction system, and an IR spectrum was measured. As a result, the level of absorption around 2270 cm$^{-1}$ based on NCO group was below the detection limit, and absorption at 1720 to 1750 cm$^{-1}$ based on C=O group was observed. Accordingly, the reaction was stopped. The reaction solution was cooled to room temperature to give 51.1 g of a light-yellow transparent liquid product. The product was measured for $^1$H-NMR. As a result, it was found that the same blocked isocyanate compound as produced in Example 1 was produced. As a result of LC analysis (1), it was found that the content of 3,5-dimethylpyrazole was 15.8% by weight. Further, the product was subjected to GC analysis and was found to have a BHT content of 10350 ppm.

Example 10

The blocked isocyanate compound (753.84 g, 3.00 mol) synthesized by the process described in Example 1, 3,5-dimethylpyrazole (29.13 g, 0.300 mol), and BHT (0.6 g, 2.54 mmol) were charged into a 1000-ml four-necked flask equipped with a stirrer, a thermometer, a dropping funnel, and a reflux condenser, and the contents of the flask were stirred in a water bath for one hr while regulating the internal temperature at 80° C. Next, 2-isocyanatoethyl methacrylate (31.03 g, 0.2 mol) was added dropwise through the dropping funnel over a period of 90 min. Upon the dropwise addition, the internal temperature of the flask changed from 80° C. to 83° C. After the completion of the dropwise addition, stirring was continued at an internal temperature in the range of 30° C. to 40° C. for one hr while regulating the temperature in a water bath. A small amount of a sample was obtained from within the reaction system, and an IR spectrum was measured. As a result, the level of absorption around 2270 cm$^{-1}$ based on NCO group was below the detection limit, and absorption at 1720 to 1750 cm$^{-1}$ based on C=O group was observed. Accordingly, the reaction was stopped. The reaction solution was cooled to room temperature to give 814.6 g of a light-yellow transparent liquid product. The product was measured for $^1$H-NMR. As a result, it was found that the same blocked isocyanate compound as produced in Example 1 was produced. As a result of LC analysis (1), it was found that the content of 3,5-dimethylpyrazole was 15.8% by weight. Further, the product was subjected to GC analysis and was found to have a BHT content of 10350 ppm.

Example 11

3,5-Dimethylpyrazole (19.81 g, 0.204 mol) and p-methoxyphenol (0.005 g, 0.04 mmol) were charged into a 100-ml four-necked flask equipped with a stirrer, a thermometer, a dropping funnel, and a reflux condenser under a nitrogen atmosphere, and the contents of the flask were cooled in a water bath of 15° C. with stirring. Next, 2-isocyanatoethyl acrylate (28.23 g, 0.2 mol) was added dropwise through the dropping funnel over a period of 90 min. Upon the dropwise addition, the internal temperature of the flask changed from 15° C. to 40° C. After the completion of the dropwise addition, stirring was continued at an internal temperature in the range of 30° C. to 40° C. for one hr while regulating the temperature in a water bath. A small amount of a sample was obtained from within the reaction system, and an IR spectrum was measured. As a result, the level of absorption around 2270 cm$^{-1}$ based on NCO group was below the detection limit, and absorption at 1720 to 1750 cm$^{-1}$ based on C=O group was observed. Accordingly, the reaction was stopped. The reaction solution was cooled to room temperature to give 48.0 g of a light-yellow transparent liquid product. The product was measured for $^1$H-NMR. As a result, it was found that a blocked isocyanate compound represented by the following formula was produced. As a result of LC analysis (1), it was found that the content of 3,5-dimethylpyrazole was 0.78% by weight. Further, the product was subjected to GC analysis and was found to have a p-methoxyphenol content of 100 ppm.

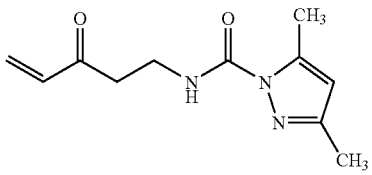

Example 12

The blocked isocyanate compound (16.13 g) synthesized in Example 11, 3,5-dimethylpyrazole (19.81 g, 0.204 mol) and p-methoxyphenol (0.005 g, 0.04 mmol) were charged into a 100-ml four-necked flask equipped with a stirrer, a thermometer, a dropping funnel, and a reflux condenser under a nitrogen atmosphere, and the contents of the flask were cooled in a water bath of 15° C. with stirring. A previously prepared mixed solution composed of 2-isocyanatoethyl acrylate (28.23 g, 0.2 mol) and p-methoxyphenol (0.005 g, 0.04 mmol) was added dropwise to the cooled solution through the dropping funnel over a period of 90 min. Upon the dropwise addition, the internal temperature of the flask changed from 15° C. to 40° C. After the completion of the dropwise addition, stirring was continued at an internal temperature in the range of 30° C. to 40° C. for one hr while regulating the temperature in a water bath. A small amount of a sample was obtained from within the reaction system, and an IR spectrum was measured. As a result, the level of absorption around 2270 cm$^{-1}$ based on NCO group was below the detection limit, and absorption at 1720 to 1750 cm$^{-1}$ based on C=O group was observed. Accordingly, the reaction was stopped. The reaction solution was cooled to room temperature to give 61.1 g of a light-yellow transparent liquid product. The product was measured for $^1$H-NMR. As a result, it was found that the same blocked isocyanate compound as produced in Example 11 was produced. As a result of LC analysis (1), it was found that the content of 3,5-dimethylpyrazole was 0.79% by weight. Further, the product was subjected to GC analysis and was found to have a 4-methoxyphenol content of 1000 ppm.

Example 13

A reaction was carried out in the same manner as in Example 1, except that methacryloyl isocyanate (22.22 g, 0.2 mol) was used instead of 2-isocyanatoethyl methacrylate. When the level of absorption around 2270 cm$^{-1}$ based on NCO group was below the detection limit and absorption at 1720 to 1750 cm$^{-1}$ based on C=O group was observed, the reaction was stopped. The reaction solution was cooled to room temperature to give 42.0 g of a light-yellow transparent liquid product. The product was measured for $^1$H-NMR. As a result, it was found that a blocked isocyanate compound represented by the following formula was produced. As a result of LC analysis (1), it was found that the content of 3,5-dimethylpyrazole was 0.92% by weight. Further, the product was subjected to GC analysis and was found to have a BHT content of 5000 ppm.

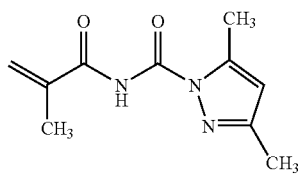

Example 14

A reaction was carried out in the same manner as in Example 1, except that diethyl pyrazole-3,5-dicarboxylate (43.3 g, 0.202 mol) was used instead of 3,5-dimethylpyrazole. When the level of absorption around 2270 cm$^{-1}$ based on NCO group was below the detection limit and absorption at 1720 to 1750 cm$^{-1}$ based on C=O group was observed, the reaction was stopped. The reaction solution was cooled to room temperature to give 74.3 g of a light-yellow transparent liquid product. The product was measured for $^1$H-NMR. As a result, it was found that a blocked isocyanate compound represented by the following formula was produced. As a result of LC analysis (1), it was found that the content of diethyl pyrazole-3,5-dicarboxylate was 0.57% by weight. Further, the product was subjected to GC analysis and was found to have a BHT content of 13000 ppm.

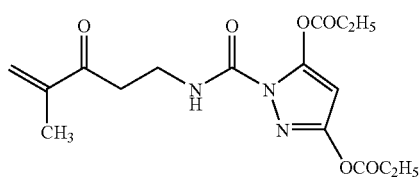

Example 15

The blocked isocyanate compound (16.75 g, 0.067 mol) synthesized by the process described in Example 1, 3,5-dimethylpyrazole (19.42 g, 0.200 mol), and BHT (0.2 g, 0.84 mmol) were charged into a 100-ml four-necked flask equipped with a stirrer, a thermometer, a dropping funnel, and a reflux condenser, and the contents of the flask were stirred at room temperature for one hr. Next, 2-isocyanatoethyl methacrylate (31.03 g, 0.2 mol) was added dropwise to the flask through the dropping funnel over a period of 90 min. Upon the dropwise addition, a rise in internal temperature of the flask was observed. Specifically, the internal temperature of the flask changed from 25° C. to 40° C. After the completion of the dropwise addition, stirring was continued at an internal temperature in the range of 30° C. to 40° C. for one hr while regulating the temperature in a water bath. A small amount of a sample was obtained from within the reaction system, and was subjected to LC analysis (1). As a result, the level of 3,5-dimethylpyrazole was below the detection limit. Accordingly, the reaction was stopped, and the reaction solution was cooled to room temperature. The product was measured for an IR spectrum. As a result, absorption around 2270 cm$^{-1}$ based on NCO group was slightly detected, and absorption at 1720 to 1750 cm$^{-1}$ based on C=O group was observed. The product obtained was 67.9 g of a liquid product that was light yellow and transparent at room temperature. The product was measured for $^1$H-NMR. As a result, it was found that the same blocked isocyanate compound as produced in Example 1 was produced. As a result of LC analysis (2), it was found that the content of 2-isocyanatoethyl methacrylate was 900 ppm. Further, the product was subjected to GC analysis and was found to have a BHT content of 4440 ppm.

The invention claimed is:

1. A process for producing a blocked isocyanate compound represented by general formula (III):

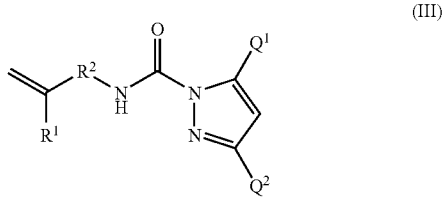

wherein $R^1$ represents a hydrogen atom or a methyl group; $R^2$ represents —CO— or —COOR$^3$— wherein $R^3$ represents an alkylene group having 2 to 6 carbon atoms; and $Q^1$ and $Q^2$ each independently represent a hydrogen atom, an alkyl group having 1 to 6 carbon atoms, RCONH—, or ROCO— wherein R represents an alkyl group having 1 to 6 carbon atoms, said process being characterized by comprising reacting a pyrazole compound (I) represented by general formula (I):

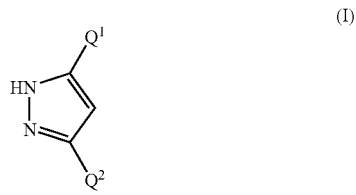

wherein $Q^1$ and $Q^2$ are as defined above,
with an ethylenically unsaturated group-containing isocyanate compound (II) represented by general formula (II):

wherein $R^1$ and $R^2$ are as defined above,
at a temperature in the range of 0° C. to 90° C. and the blocked isocyanate compound represented by general formula (III) is used as a solvent or a dispersant for one or both of the pyrazole compound (I) and the ethylenically unsaturated group-containing isocyanate compound (II) introduced at the beginning of the reaction.

2. The process according to claim 1, characterized in that the ethylenically unsaturated group-containing isocyanate compound (II) is added to the pyrazole compound (I) dissolved or dispersed in the blocked isocyanate compound (III).

3. The process according to claim 1, characterized in that the ethylenically unsaturated group-containing isocyanate compound (II) dissolved or dispersed in the blocked isocyanate compound (III) is added to the pyrazole compound (I).

4. The process according to claim 1, characterized in that the ethylenically unsaturated group-containing isocyanate compound (II) dissolved or dispersed in the blocked isocyanate compound (III) is added to the pyrazole compound (I) dissolved or dispersed in the blocked isocyanate compound (III).

5. The process according to claim 1, characterized in that the pyrazole compound (I) is added to the ethylenically unsaturated group-containing isocyanate compound (II) dissolved or dispersed in the blocked isocyanate compound (III).

6. The process according to claim 1, characterized in that the pyrazole compound (I) dissolved or dispersed in the blocked isocyanate compound (III) is added to the ethylenically unsaturated group-containing isocyanate compound (II).

7. The process according to claim 1, characterized in that the pyrazole compound (I) dissolved or dispersed in the blocked isocyanate compound (III) is added to the ethylenically unsaturated group-containing isocyanate compound (II) dissolved or dispersed in the blocked isocyanate compound (III).

8. The process according to claim 1, characterized in that the pyrazole compound (I) dissolved or dispersed in the blocked isocyanate compound (III) and the ethylenically unsaturated group-containing isocyanate compound (II) dissolved or dispersed in the blocked isocyanate compound (III) are simultaneously added to a reactor.

9. The process according to claim 1, wherein $Q^1$ and $Q^2$ represent an alkyl group having 1 to 5 carbon atoms.

10. The process according to claim 1, wherein $R^2$ represents —COOR$^3$— wherein $R^3$ represents an alkylene group having 2 to 6 carbon atoms.

11. The process according to claim 1, characterized in that the pyrazole compound (I) is reacted with the ethylenically unsaturated group-containing isocyanate compound (II) in the presence of a polymerization inhibitor.

12. The process according to claim 11, characterized in that the polymerization inhibitor is used in an amount of 10 to 20000 ppm based on the blocked isocyanate compound (III).

13. The process according to claim 1, characterized in that the pyrazole compound (I) is reacted in an amount of 0.5 to 2.0 times by mole the amount of the ethylenically unsaturated group-containing isocyanate compound (II).

* * * * *